US010538369B2

(12) United States Patent
Ritsche

(10) Patent No.: US 10,538,369 B2
(45) Date of Patent: Jan. 21, 2020

(54) LIQUID DISPENSER

(71) Applicant: APTAR RADOLFZELL GMBH, Radolfzell (DE)

(72) Inventor: Stefan Ritsche, Eigeltingen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 275 days.

(21) Appl. No.: 14/430,804

(22) PCT Filed: Aug. 28, 2013

(86) PCT No.: PCT/EP2013/067847
§ 371 (c)(1),
(2) Date: Mar. 24, 2015

(87) PCT Pub. No.: WO2014/048668
PCT Pub. Date: Apr. 3, 2014

(65) Prior Publication Data
US 2015/0274386 A1 Oct. 1, 2015

(30) Foreign Application Priority Data
Sep. 25, 2012 (DE) .......................... 10 2012 217 338

(51) Int. Cl.
*B65D 47/28* (2006.01)
*B05B 11/00* (2006.01)
(Continued)

(52) U.S. Cl.
CPC .......... *B65D 47/283* (2013.01); *A61F 9/0008* (2013.01); *B05B 11/0067* (2013.01);
(Continued)

(58) Field of Classification Search
CPC .............. B65D 47/283; B05B 11/0067; B05B 11/0072
(Continued)

(56) References Cited

U.S. PATENT DOCUMENTS 5,154,325 A * 10/1992 Ryder ................. B05B 11/0021
222/189.06
5,183,184 A * 2/1993 Ranalletta ........... B05B 11/0021
222/189.09
(Continued)

FOREIGN PATENT DOCUMENTS

DE          102 01 110 B4    10/2003
DE    10 2009 006 428 A1      8/2010
(Continued)

OTHER PUBLICATIONS

International Search Report of European Patent Office issued in International Application No. PCT/EP2013/067847 with English translation dated Nov. 29, 2013 (4 pages).
(Continued)

*Primary Examiner* — Jeremy Carroll
(74) *Attorney, Agent, or Firm* — Flynn Thiel, P.C.

(57) ABSTRACT

Liquid dispenser for discharging pharmaceutical liquids, having a housing, an outlet opening and an outlet valve assigned to the outlet opening. The outlet valve includes a pressure chamber arranged upstream of a valve opening and delimited to one side by a valve plate of a valve body. By increasing the pressure in the pressure chamber, the valve can be opened. The pressure chamber has a flat form and has a large surface area in contact with liquid in relation to the volume.

At least one portion of the valve plate which is in contact with liquid in the pressure chamber is of a valve plate material produced using metallocenes as catalysts.

17 Claims, 4 Drawing Sheets

(51) Int. Cl.
 *B65D 65/38* (2006.01)
 *A61F 9/00* (2006.01)
 *B65D 47/20* (2006.01)
 *B05B 11/04* (2006.01)

(52) U.S. Cl.
 CPC ........ *B05B 11/0072* (2013.01); *B05B 11/047* (2013.01); *B65D 47/2068* (2013.01); *B65D 47/2081* (2013.01); *B65D 65/38* (2013.01)

(58) Field of Classification Search
 USPC ............................. 222/212, 321.2, 420, 422
 See application file for complete search history.

(56) References Cited

U.S. PATENT DOCUMENTS

| | | | | | |
|---|---|---|---|---|---|
| 5,226,568 | A | * | 7/1993 | Newton | B65D 47/2081 222/212 |
| 5,320,254 | A | * | 6/1994 | Ranalletta | B05B 11/0021 222/189.08 |
| 5,431,310 | A | * | 7/1995 | Kanner | B05B 11/0021 222/212 |
| 5,723,545 | A | * | 3/1998 | Harrington | C08F 210/02 522/160 |
| 5,979,711 | A | | 11/1999 | Fuchs et al. | |
| 6,695,173 | B1 | * | 2/2004 | Fontana | B65D 47/2068 222/206 |
| 8,517,222 | B2 | | 8/2013 | Painchaud et al. | |
| 8,616,418 | B2 | * | 12/2013 | Painchaud | B05B 11/0021 222/212 |
| 9,238,532 | B2 | | 1/2016 | Decock et al. | |
| 9,579,671 | B2 | | 2/2017 | Decock et al. | |
| 2009/0294347 | A1 | * | 12/2009 | Wochele | B05B 11/0021 210/244 |
| 2011/0068133 | A1 | | 3/2011 | Painchaud et al. | |
| 2011/0155770 | A1 | | 6/2011 | Painchaud et al. | |
| 2013/0043273 | A1 | * | 2/2013 | Lee | A61M 5/284 222/82 |

FOREIGN PATENT DOCUMENTS

| | | |
|---|---|---|
| EP | 0 791 397 A1 | 8/1997 |
| JP | 2005-171169 A | 6/2005 |
| JP | 2008-307146 A | 12/2008 |
| WO | WO 2006/043295 A1 | 4/2006 |
| WO | WO 2007/109166 A2 | 9/2007 |
| WO | WO 2009/130411 A1 | 10/2009 |
| WO | WO 2012/013894 A1 | 2/2012 |
| WO | WO 2012/084557 A1 | 6/2012 |

OTHER PUBLICATIONS

Examination Report of German Patent Office issued in Application No. 10 2012 217 338.2 dated Jan. 7, 2013 (5 pages).
English translation of Office Action of Japan Patent Office issued in Application No. 2015-533501 dated Feb. 23, 2017 (3 pages).
"TOPAS Elastomer E-140 Now Available"; Press Release dated Sep. 30, 2010 (2 pages).

* cited by examiner

LIQUID DISPENSER

FIELD OF APPLICATION AND PRIOR ART

The invention relates to a liquid dispenser for discharging pharmaceutical liquids, having a housing, an outlet opening and an outlet valve assigned to the outlet opening. In this case, the outlet valve of such a liquid dispenser of the generic type comprises, as main components, a valve opening which is connected upstream of the outlet opening or is identical to the outlet opening and a valve pin, the valve pin closing the valve opening in a closed position of the outlet valve and releasing the valve opening in an open position of the outlet valve. Furthermore, the outlet valve comprises a valve body, which has either the valve pin or the valve opening and which is displaceable at least partially with respect to the housing of the liquid dispenser in order to thereby make it possible to transfer the outlet valve between said closed position and said open position. A pressure chamber which is arranged upstream of the valve opening and is delimited to one side by a valve plate of the valve body also forms part of the valve, the valve body being displaceable at least in portions with respect to the housing by means of the application of pressure by liquid in a pressure chamber, such that the valve pin and the valve opening can thereby be displaced relative to one another.

In particular, a liquid dispenser of the generic type has a pressure chamber in which there is a particular relationship between the volume $V_{DK}$ of the pressure chamber and the pressure chamber surface area facing toward the pressure chamber on the valve body side, specifically a relationship according to which the quotient of pressure chamber volume divided by pressure chamber surface area lies in the interval of between 0.1 mm and 2.4 mm.

Liquid dispensers of the generic type serve primarily for discharging pharmaceutical liquids and are intended with particular preference for dispensing the liquid in the form of individual droplets. The outlet valve of such dispensers opens and thus enables liquid to be dispensed if there is a sufficiently high liquid pressure in the pressure chamber.

A liquid dispenser with an outlet valve which corresponds at least approximately to said parameters is known from DE 10 2009 006 428 A1. In the design proposed therein, as well as in other designs of the generic type, a pressure is generated within a liquid reservoir of the dispenser in the manner stated for the purpose of discharging liquid, for example by a direct volumetric reduction of the liquid reservoir. This pressure is then likewise established in the pressure chamber, where it acts on the valve plate. Since the latter is at least partially displaceable with respect to the housing, such a displacement takes place under the influence of this pressure, as a result of which the valve pin and the valve opening are spaced apart from one another, such that liquid can pass outward through the valve opening. In the case of the configuration as per DE 10 2009 006 428 A1, the valve pin is connected to the valve plate, whereas the valve opening is part of the housing. It is similarly also possible, however, to use a valve pin which is stationary in relation to the housing, and in respect thereto a valve opening provided on the valve body is displaced. This, too, is known in principle from the prior art.

In dispensers of the generic type, the purpose of the valve plate is in particular that of providing a comparatively large surface area, such that the desired displacement takes place already given a comparatively low excess pressure in the pressure chamber. This plays a considerable role, for example, in the case of droplet dispensers, in which it is desirable for the liquid to pass outward through the valve opening at only a low excess pressure.

The comparatively large surface area of the valve body which faces toward the valve chamber in the region of the valve plate leads to a problem, however. It has thus been established that the conventional selection of material for the valve plate, specifically the use of thermoplastic elastomers (TPE), can lead to contamination of the liquid. Particularly in the region of the pressure chamber in which that part of the liquid which is discharged over the course of one of the next application processes is stored, the comparatively large liquid contact surface on the valve body and a comparatively small volume of the pressure chamber have the effect that the contamination is at its highest in the pressure chamber. The contamination can be caused in particular by additives used in the TPE production for bringing about specific properties, for example the desired degree of deformability which may be required. These additives tend to escape in small quantities from their carrier material over time and thereby bring about said contamination. Since long periods of time can occasionally pass between discharging processes of a liquid dispenser of the generic type, an unacceptable degree of contamination can arise in the region of the pressure chamber and therefore in the part of the liquid waiting to be discharged.

It is known from the prior art, specifically EP 0791397 B1, in conjunction with discharging apparatuses for media to produce plastic components of a discharging apparatus using metallocenes.

OBJECT AND SOLUTION

It is an object of the invention to develop a liquid dispenser of the generic type to the effect that the problem relating to increased contamination in the region of the pressure chamber is reduced.

According to the invention, it is proposed in this respect according to a first aspect that at least one portion of the valve plate which is in contact with the liquid in the pressure chamber consists of a valve plate material which is a plastic produced using metallocenes as catalysts.

According to a second aspect, it is proposed that a plastic produced using metallocenes as catalysts is used at, least for a portion of the valve plate which is in contact with the liquid in the pressure chamber.

The design according to the invention of a liquid dispenser of the generic type accordingly provides that that component which forms a considerable proportion of the wall surface of the pressure chamber is produced from a plastic which has been produced using metallocene catalysts. Hereinbelow, a plastic of this type is referred to as metallocene plastic. The design according to the invention is based on the knowledge that the contamination of the liquid by additives of the plastic displays a very much greater disadvantageous effect in the region of the generically configured pressure chamber than at other liquid-carrying regions of the liquid dispenser, since firstly there is a very unfavorable relationship between the size of the wall surfaces and the liquid volume here and since secondly that liquid which is arranged in the pressure chamber is discharged during the respective next or one of the respective next discharging operations. Mixing with less contaminated parts of the liquid in the dispenser, which might lead to a reduction in the specific quantity of contamination, usually no longer takes place.

It has been found that the contamination can be prevented or reduced in an outstanding manner if at least portions of the valve plate or else the entire valve plate or the pressure chamber surface area thereof are produced from said material.

With respect to the material, reference is made to EP 0791397 B1, the disclosure of which relating to plastics produced using metallocenes and the properties thereof is incorporated herein by express reference.

Moreover, the following is furthermore to be established in addition with respect to the materials to be used according to the invention.

The plastic used according to the invention is preferably an olefinic, in particular ethylene-containing, polymer, it being possible for the polymer to be a homopolymer or copolymer. According to the invention, preference is given, however, to a copolymer, i.e. a polymer made up of at least two different monomer units.

It is furthermore preferred if the plastic used according to the invention is a copolymer comprising ethene (ethylene) as monomer unit.

In a particularly preferred embodiment, the plastic used according to the invention is a cycloolefin copolymer, i.e. a copolymer comprising at least one, in particular one, cycloolefin as monomer unit.

Cycloolefin copolymers are particularly advantageously distinguished in particular by the fact that they can be produced with a very high degree of purity, as a result of which the above-described risk of contamination can be minimized considerably.

In a further embodiment, the plastic used according to the invention can be a cycloolefin copolymer which is produced (by copolymerization) from a cycloolefin such as, for example, norbornene and an alpha olefin such as, for example, ethene (ethylene). The alpha olefin can be present in a proportion of at least 5% by weight and at most 40% by weight, in particular of at least 5% by weight and at most 30% by weight, based on the total weight of the cycloolefin copolymer.

Copolymers made up of norbornene and ethene monomer units are commercially available under the name Topas.

In an alternative embodiment, the plastic used according to the invention is polypropylene.

As already mentioned, the plastic used according to the invention is produced by means of metallocenes as catalysts. Suitable metallocene catalysts can be selected from the group consisting of alkali metallocenes, alkaline earth metallocenes, metallocenes comprising metal atoms from subgroups four to twelve of the Periodic Table of Elements and combinations thereof.

In particular, suitable metallocene catalysts can be selected from the group consisting of titanocene, zirconocene, vanadocene, chromocene, manganocene, ferrocene, cobaltocene, nickelocene, zincocene, niobocene, molybdocene, ruthenocene, rhodocene, tantalocene, tungstocene, rhodocene, osmocene, iridocene, platinocene and combinations thereof.

The metallocenes can be provided in particular as cocatalysts.

The metallocenes are preferably present in the plastic in a weight proportion of less than 5/10000000, in particular less than 1/10000000.

The metallocene catalysts can remain in the component or can also be separated therefrom again after the production thereof.

It is conventionally the case that the metallocene catalysts initiate and in particular accelerate the polymerization process required for producing the plastic, the metallocene catalysts also being responsible in particular for a very tight molar mass distribution of the polymer or plastic which forms.

In an advantageous embodiment, the plastic used according to the invention, possibly apart from potential metallocene traces which are negligible from a medical or pharmaceutical point of view, does not contain any further additives. The risk of contamination can thereby be additionally reduced.

The interval mentioned, in which the quotient of pressure chamber volume to pressure chamber surface area lies according to the invention, corresponds approximately to the gap width within the pressure chamber. This gap therefore preferably has approximately a width of between 0.1 mm and 2.4 mm. The smaller the volume, the more expedient the configuration according to the invention of the valve plate. A quotient lying between 0.2 mm and 1.0 mm in particular has proved to be particularly advantageous in practice.

The upper limit value of 2.4 mm here is qualified by the fact that a gap width in this region or a smaller gap width has the effect that only a small quantity of air, which might have a negative effect on the discharging process, remains in the pressure chamber. An average gap width of less than or equal to 1.0 mm has the effect that the liquid does not flow or flows only to a small extent out of the pressure chamber back into the liquid reservoir even when the dispenser is stored in an orientation in which the pressure chamber is arranged above the liquid reservoir connected thereto. It is therefore the case that no air or only a small quantity of air penetrates into the pressure chamber in such an orientation, and this in turn is advantageous for improved discharging characteristics. The reduced flow of liquid out of the pressure chamber into the liquid reservoir is presumably attributable to a capillary effect in the pressure chamber.

In absolute numbers, it is considered to be particularly advantageous if the pressure chamber volume is between 20 $mm^3$ and 100 $mm^3$, in particular between 30 $mm^3$ and 50 $mm^3$.

In this respect, it is to be noted that the pressure chamber volume is considered to be that volume which is reached as intended by liquid in the valve region and which in this respect extends from a pressure chamber inlet as far as the valve opening which is closed by the valve pin. In this respect, the pressure chamber inlet is that point of the liquid path from a liquid reservoir of the dispenser as far as the pressure chamber at which the cross-sectional area of the liquid path is at its minimum.

A size of between 100 $mm^2$ and 300 $mm^2$ is considered to be a particularly advantageous value for the size of the pressure chamber surface area of the valve body, i.e. that surface which is formed at least in part by metallocene plastics. In this respect, the pressure chamber surface area is considered to be the totality of those surfaces which are located on the part of the valve body moved in the course of opening and closing and, if appropriate, the valve pin assigned thereto and which directly delimit the pressure chamber when the outlet valve is closed.

As has already been mentioned in the introduction, two different designs are conceivable in principle with respect to the arrangement of the valve plate. On the one hand, the latter can bear the valve pin and thus make the latter displaceable with respect to the valve opening fixed to the housing. On the other hand, the valve opening can also be displaced together with the valve plate, with the valve pin being arranged fixed to the housing in this case. The use of the metallocene plastic does not necessarily have to be limited to the valve plate and, if appropriate, additionally the valve pin. It is particularly advantageous if further surfaces which are immovable with respect to the outer housing of the liquid dispenser and which delimit the pressure chamber are also produced at least in part from such a plastic or are configured with a layer made of such a plastic. It is preferable for at least 30% of the surfaces which delimit the pressure chamber to consist of metallocene plastic.

Configuring the liquid dispenser entirely or predominantly of metallocene plastic is at least preferably not provided, however. In particular, it is preferable that an outer housing of the liquid dispenser and preferably also those walls which delimit the liquid reservoir of the dispenser are not produced from the metallocene plastic of comparatively complex production.

One possibility for embodying the mobility of the valve body consists in configuring the latter as a comparatively rigid component which at least as intended is not in need of deformation and which is displaceable as a whole with respect to the housing. In the case of such a design, it would accordingly be provided that the valve body which is displaceable as a whole is displaceable in translation with respect to portions fixed to the housing with a sliding guide or the like. An alternative thereto provides that, for the purpose of making it possible for the valve opening or the valve pin to be displaced with respect to the housing, the valve body has an intrinsically deformable configuration and is fixed to the housing in a fixing region on the outside. In this case, the deformability can be provided, alternatively to one another, in a region which consists of the metallocene plastic or else in a region which consists of a plastic differing therefrom.

In order to achieve the desired deformability to a sufficient extent, it has been found to be advantageous if provision is made, in the region of the valve plate, of a circumferential deformation region, in which the valve plate has a thinner-walled form than in regions adjoining radially on the inside and outside. In particular, at its thinnest point the circumferential region of preferably bead-like form is at most 60% as thick as the regions formed with maximum thickness on the inside and outside of the bead.

In principle, it is possible to bring about a restoring force of the outlet valve into its closed position through elasticity of the valve component, either the elasticity of the metallocene plastic or the elasticity of a different part of the different plastic which forms certain portions of the valve plate. It is advantageous, however, if a separate valve spring is provided for producing the restoring force, said valve spring subjecting the outlet valve to force in the direction of the closed position thereof. The valve spring is accordingly arranged in such a way that it subjects the valve pin to force in the direction of the valve opening or subjects the valve opening to force in the direction of the valve pin. Through the use of such a separate valve spring, the desired closing force does not have to be taken into consideration when selecting the material of the valve body. It suffices if the valve body is movable as a whole or portions thereof are adequately deformable.

In order to avoid a situation where said valve spring is supported on the highly deformable regions of the valve body, it is advantageous if the valve body has a supporting body, which is displaceable together with the valve pin or the valve opening and which consists of a plastic which is more rigid than the material or the materials of the valve plate, for example polyethylene and/or polypropylene. This achieves an improved introduction of the spring force of the valve spring into the valve body. The metallocene plastic can then be provided in the manner of a coating over the supporting body.

A liquid dispenser according to the invention serves in particular for dispensing pharmaceutical liquids. It is therefore preferably filled with such a liquid, in particular with an ophthalmic liquid. In particular, the liquids are pharmaceutical liquids for treating increased pressure within an eye (glaucoma treatment), for treating dry eyes and for treating allergies and inflammations. As constituents, these liquids preferably contain active ingredients selected from the group consisting of alpha-2 agonists, e.g. brimonidine, prostaglandin analogs (tafluprost, latanoprost, bimatoprost, travoprost), beta blockers, e.g. timolol, and carboanhydrase inhibitors, e.g. dorzolamide or hyaluronic acid compounds, film formers, e.g. methyl cellulose compounds and cyclosporine or antihistamines, e.g. olopatadine and levocabastine, steroids, e.g. loteprednol and dexamethasone, and NSAID, e.g. keterolac, and combinations thereof.

BRIEF DESCRIPTION OF THE DRAWINGS

Further aspects and advantages of the invention become apparent from the following description of preferred embodiments of the invention, which are explained with reference to the figures, in which.

DETAILED DESCRIPTION OF THE EMBODIMENTS

Figure 1:
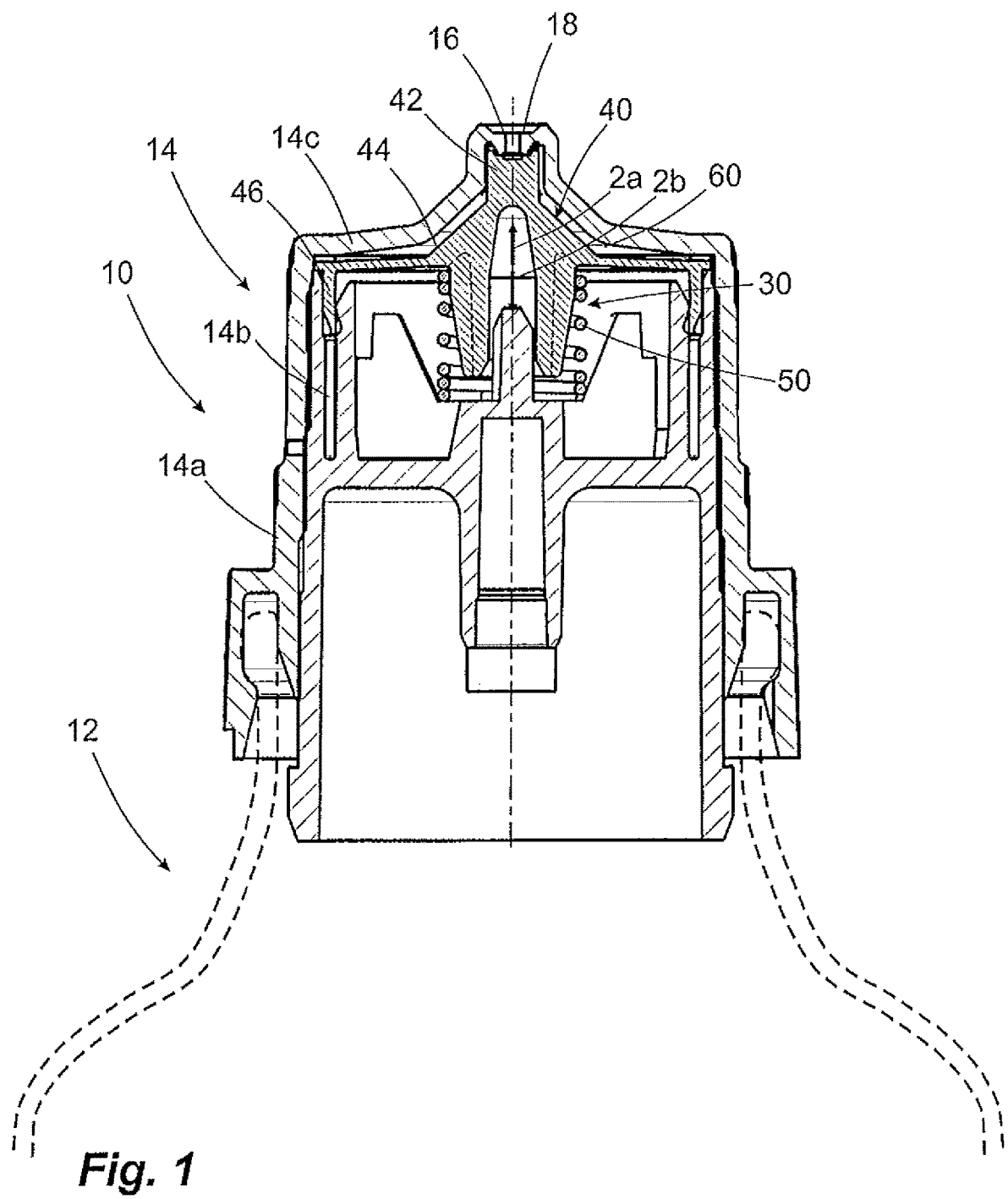
FIGS. 1 to 3 show liquid dispensers according to the invention, or the discharge heads thereof, with a valve pin which is displaceable with respect to an outer housing.

FIG. 1 shows a first liquid dispenser 10 according to the invention intended for discharging a pharmaceutical liquid in droplet form. This may be a pharmaceutical liquid for treating eyes of a patient, for example.

The liquid dispenser 10 comprises a bottle vessel 12, which serves as a liquid reservoir, and a discharge head 14. The discharge head 14 is provided with a discharge opening 16, which at the same time represents a valve opening 16 of an outlet valve 30 and which pierces through an outer housing 14a of the discharge head 14. The outlet valve 30 is configured as an outlet valve 30 which opens in a pressure-dependent manner.

For this purpose, a valve body 40 is arranged below the valve opening 16, with respect to the illustration of FIG. 1, said valve body having a valve pin 42 which is movable with respect to the outer housing 14a and which is arranged on the valve body 40 in such a manner that it can close the valve opening 16 in a closed position of the outlet valve 30. Furthermore, the valve body 40 has a valve plate 44, which has a thin-walled configuration in order to ensure deformability of the valve body 40 in a manner explained further hereinbelow. On the outside, the valve body 40 is delimited by a fixing web 46, which is fastened in a retaining groove 14b of the housing of the discharge head 14. A valve spring 50 supported by way of its bottom end on the housing of the discharge head 14 presses the valve pin 42 permanently in the direction of the arrow 2a and therefore in the direction of the closed position, in which it bears against an edge surrounding the valve opening 16 and thereby closes the outlet valve 30.

The housing of the discharge head 14 is matched to the shape of the valve body 40 and the valve plate 44 thereof in an end wall region 14c in such a manner that a pressure chamber 60 of the outlet valve 30 having a very small volume remains between said end wall and the valve body 44. The distance between the inner side of the housing wall in the end wall region 14c and the valve plate 44 of the valve component 40 is approximately 0.2 mm. That part of the surface area of the valve component 40 which is in contact with the contents of the pressure chamber 60 and in the sense of this document forms the pressure chamber surface area has a size of approximately 200 mm$^2$. The internal volume of the pressure chamber 60 is approximately 40 mm$^3$. The pressure chamber is connected to the liquid reservoir by a duct (not shown in more detail).

To operate the liquid dispenser 10, it is provided in the case of the configuration of FIG. 1 to manually press the bottle vessel 12 together, resulting in an increase in pressure both in the liquid reservoir and in the pressure chamber 60. As a response to this increase in pressure in the pressure chamber 60, the predominant part of the valve body 40 is displaced with respect to the housing 14a in the direction of the arrow 2b, such that the valve pin 42 is also detached from the edge surrounding the valve opening 16 and thus opens the outlet valve 30. On account of the comparatively large areal extent of the valve plate 44, this requires only a small excess pressure. Since this small excess pressure is already sufficient, the liquid passes in virtually pressureless form through the valve and discharge opening 16, this therefore being advantageous in the specific case since the liquid dispenser 10 of FIG. 1 is in the form of a droplet dispenser which is to be used turned over and in which it is provided that the emerging liquid firstly accumulates on a droplet-forming surface 18 on the outer side of the valve and discharge opening 16 and is only detached therefrom when a desired droplet size has been reached. A spray jet resulting from an excessively high outlet pressure is not desired on account of this specific function.

The pressure chamber 60 is naturally that part of the liquid-carrying components of the liquid dispenser 10 in which that liquid which is discharged during the respective next discharging process or one of the next discharging processes is arranged. Since this liquid has passed constantly into the pressure chamber 60 in the course of the respective preceding operations, it occasionally resides therein for a very long period of time, for example for a number of days, if the dispenser is not used for such a period of time. Since, moreover, only a small volume of liquid is present in the pressure chamber 60 and bears against comparatively large wall surfaces of the dispenser 10 produced from plastic over a long period of time, the liquid dispenser 10 as shown in FIG. 1 is designed to the effect that it prevents contamination of said quantity of liquid with components which escape from the plastics, in particular various additives. For this purpose, it is provided that the valve body 40 of the configuration of FIG. 1 consists entirely of a plastic which has been produced using metallocenes as catalyst.

The plastic is preferably a cycloolefin copolymer, in particular a copolymer which is made up of ethene and norbornene monomer units. A copolymer of this type is commercially available under the name Topas. A plastic of this type comprises only a comparatively small quantity of additives or has a low tendency to release additives into the pressure chamber.

This has the effect that no additives pass into the liquid in the pressure chamber 60 or additives pass into the liquid in the pressure chamber 60 only to a small extent at least on the part of the valve body. Even if the liquid resides in the pressure chamber 60 for a long period of time, there is therefore no contamination on a problematic scale.

In a variant (not shown) to the configuration of FIG. 1, the inner side of the end face wall 14c, which adjoins the pressure chamber 60, can also be coated with a coating made of the same plastic or a different plastic produced using metallocenes as catalyst, such that an even greater proportion of those surfaces which directly delimit the pressure chamber is largely uncritical in respect of contamination. However, the use of such plastics is advantageous particularly in the region of the valve body, since it is thereby possible to achieve the desired deformability of the valve plate 44 without having to accept the disadvantages of the various additives of thermoplastic elastomers customarily used here.

Figure 2:
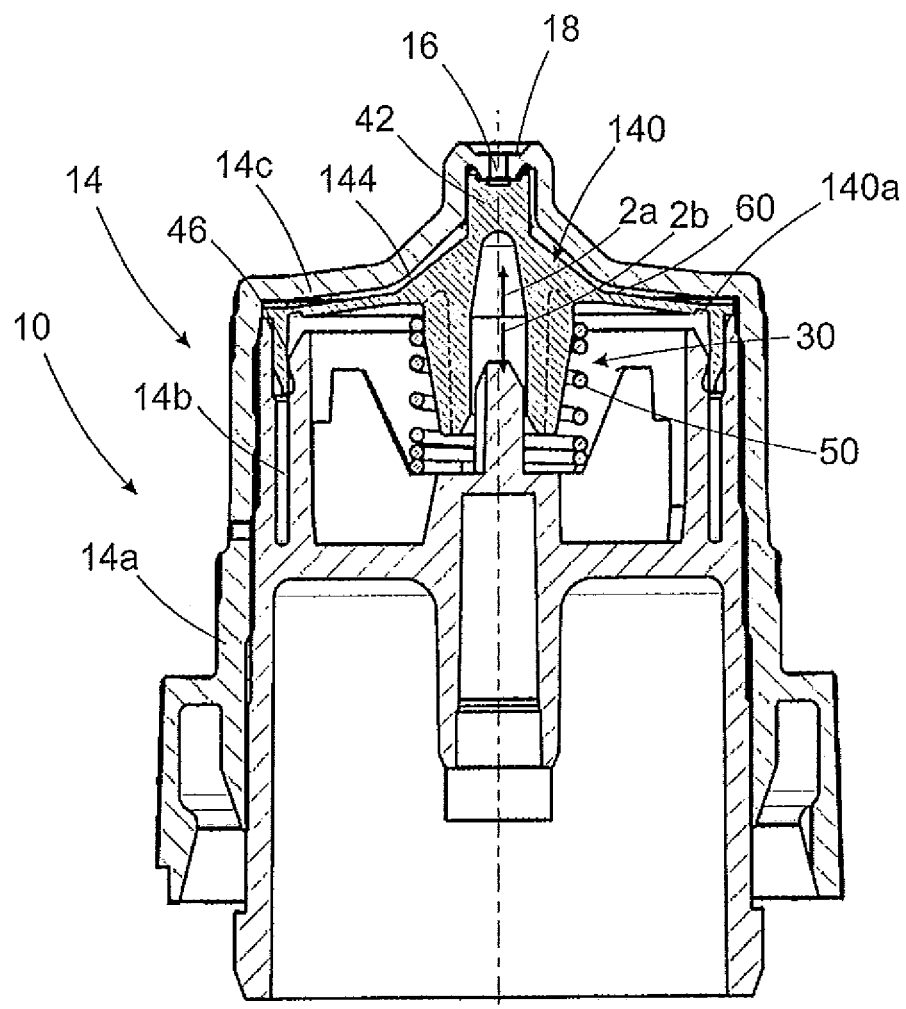

The configuration shown in FIG. 2 differs from the configuration shown in FIG. 1 in that, in order to achieve an even more effortless deformability of the valve body 140, a bead 140a is introduced into the edge region thereof. The deformation of the valve body 140 which is required during the course of changing between the closed position and the open position is therefore effected predominantly in the region of this bead 140a. This makes it possible, when designing the metallocene-catalyst-based plastic used for the valve body 140, not to have to place special emphasis on the deformability in thicker-walled regions when configuring the plastic. For the rest, the mode of operation of the configuration shown in FIG. 2 corresponds to that shown in FIG. 1.

Figure 3:
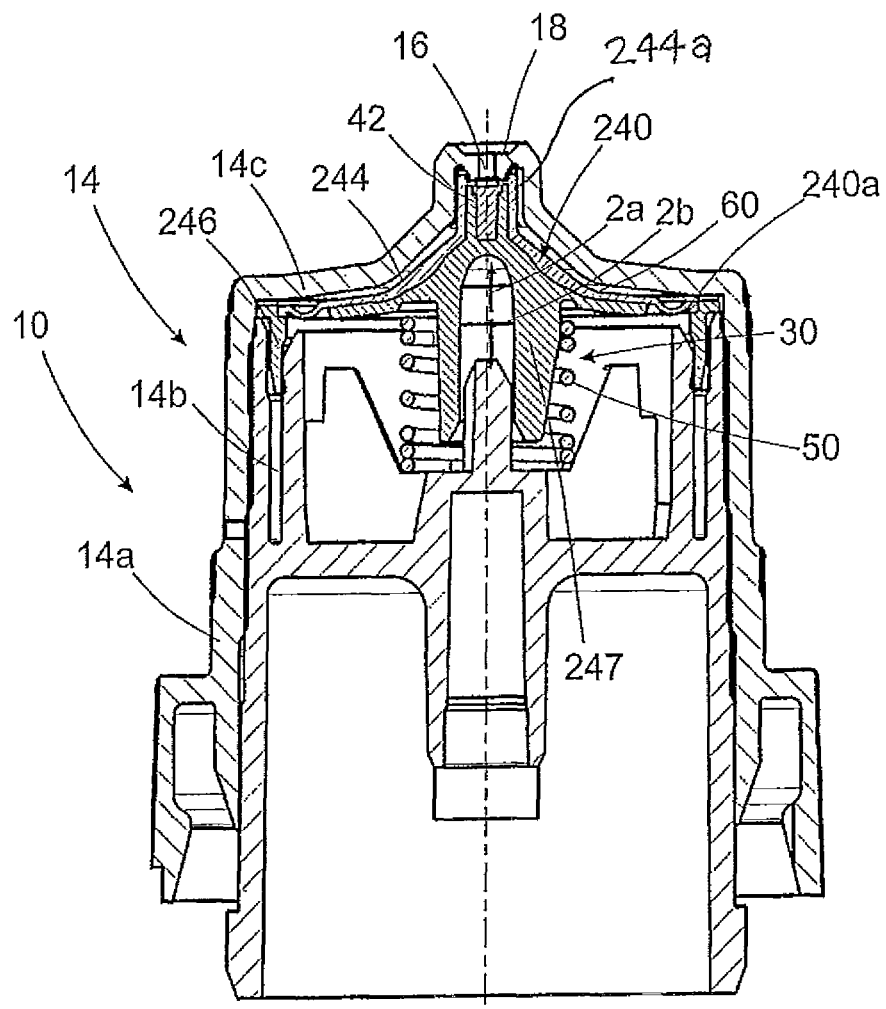

The configuration of FIG. 3 shows a variation in which the valve body 240 has an even more complex design, specifically in that it consists of two different plastics, which can be joined together for example by multi-component injection molding. Whereas the predominant part of the pressure chamber surface area of the valve body 240 which is in direct contact with the liquid in the pressure chamber 60, and in particular the valve plate 244 together with the bead 240a and a central portion 244a of the valve plate 244 which covers the pin 42, consists again of plastic which has been produced by means of metallocene catalysts, both the fastening web 246 and a centrically arranged supporting component 247 are produced from a more rigid plastic, which, in the case of the web 246, allows for more simple joining of the components during assembly, and, in the case of the supporting component 247, ensures a more extensive introduction of the valve spring force into the valve body 240.

Figure 4:
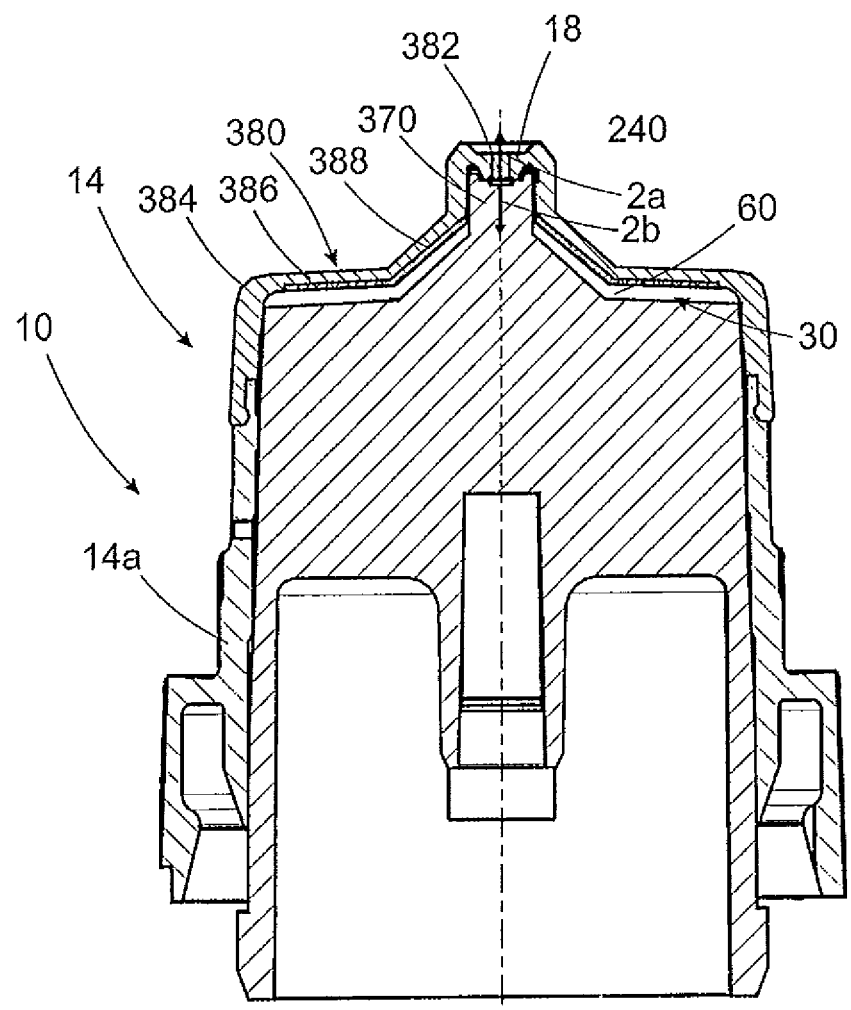
FIG. 4 shows a variant thereto with a valve opening which is displaceable with respect to the outer housing.

The configuration of FIG. 4 differs considerably from the preceding embodiments, since here, in a manner differing from the preceding embodiments, the valve pin 370 is provided immovably in relation to the housing 14a of the discharge head 14.

In the case of the configuration of FIG. 4, the displaceable valve body 380 forms the end face of the dispenser, such that the valve opening 382 is lifted from the stationary valve pin 370 in the direction of the arrow 2a in the event that a pressure is applied to the pressure chamber 60. The valve body 380 is produced entirely from plastics with adequate deformability, in order to allow the valve opening 382 to be lifted. The valve body 380 is in this respect sufficiently elastic to itself provide the restoring force in the direction of the closed position. Alternatively, however, a separate valve spring can be provided here, too. This would then act on the end face of the dispenser from above in the direction of the arrow 2b.

The valve body 380 consists of two different plastic materials. Thus, an outer shell 384 is produced from a conventional plastic, for example a thermoplastic elastomer, whereas a coating 388 applied to the inner side of the valve plate 386 of the valve body 384 consists in turn of a plastic selected from the aforementioned plastics, for the production of which metallocenes are used as catalysts. This in turn considerably reduces the risk of contamination of those proportions of liquid which are arranged in the pressure chamber 60.

The invention claimed is:

1. A liquid dispenser for discharging pharmaceutical liquids, comprising:
   a housing;
   an outlet opening; and
   an outlet valve assigned to the outlet opening;
   wherein the outlet valve comprises:
      a valve opening and a valve pin, the valve pin closing the valve opening in a closed position of the outlet valve and releasing the valve opening in an open position of the outlet valve;
      a valve body, which has either the valve pin or the valve opening and which is displaceable at least partially with respect to the housing of the liquid dispenser in order to thereby allow for transfer of the outlet valve between the closed position and the open position; and
      a pressure chamber, which is arranged upstream of the valve opening and is delimited to one side by a valve plate of the valve body, the valve body being displaceable at least in portions by application of pressure at the valve plate by liquid in the pressure chamber, such that the valve pin and the valve opening are thereby displaced relative to one another;
   wherein at least one portion of the valve plate which is in contact with liquid in the pressure chamber comprises a valve plate material which is a plastic produced using metallocenes as catalysts;
   wherein the plastic is an elastic cycloolefin copolymer or a combination of an elastic cycloolefin copolymer and polypropylene; and
   wherein the valve body has an intrinsically deformable configuration and has a fixing region on an outside which is fixed immovably in relation to the housing for allowing the valve opening or the valve pin to be displaced with respect to the housing.

2. The liquid dispenser as claimed in claim 1, wherein the pressure chamber has a pressure chamber volume $V_{DK}$ and the valve body has a pressure chamber surface area $A_{DK}$ facing toward the pressure chamber, and the quotient of pressure chamber volume $V_{DK}$ divided by pressure chamber surface area $A_{DK}$ lies in the following interval:

$$0.1 \text{ mm} \leq V_{DK}/A_{DK} \leq 2.4 \text{ mm}.$$

3. The liquid dispenser as claimed in claim 2, wherein the quotient of pressure chamber volume $V_{DK}$ and pressure chamber surface area $A_{DK}$ lies in the following interval:

$$0.2 \text{ mm} \leq V_{DK}/A_{DK} \leq 1.0 \text{ mm}.$$

4. The liquid dispenser as claimed in claim 2, wherein the pressure chamber volume $V_{DK}$ is between 20 mm$^3$ and 100 mm$^3$.

5. The liquid dispenser as claimed in claim 2, wherein the pressure chamber surface area $A_{DK}$ of the valve body measures between 100 mm$^2$ and 300 mm$^2$.

6. The liquid dispenser as claimed in claim 2, wherein the pressure chamber volume $V_{DK}$ is between 30 mm$^3$ and 50 mm$^3$.

7. The liquid dispenser as claimed in claim 1, wherein the valve opening is provided immovably in relation to the housing and the valve body has the valve pin, the valve pin being displaceable by at least partial displacement of the valve plate with respect to the valve opening.

8. The liquid dispenser as claimed in claim 7, wherein at least one portion of the valve plate and the valve pin are in the form of an integral component made of the plastic produced using metallocenes.

9. The liquid dispenser as claimed in claim 1, wherein the valve plate is provided with a circumferential deformation region, in which the valve plate has a thinner form than in regions adjoining radially on an inside and outside.

10. The liquid dispenser as claimed in claim 1, wherein the outlet valve has a valve spring, which subjects the valve pin and the valve opening to force in a direction of the closed position.

11. The liquid dispenser as claimed in claim 1, wherein the valve body has a supporting body, which is displaceable together with the valve plate and which consists of a plastic which is more rigid than the valve plate material.

12. The liquid dispenser as claimed in claim 1, wherein the valve opening is immovable relative to the housing and the valve pin forms part of the valve body and is displaceable along with the valve plate relative to the valve opening, and the valve plate has a central portion disposed to substantially cover the valve pin, the central portion being formed integrally and as one-piece with said valve plate from the plastic produced using metallocenes.

13. A liquid dispenser for discharging pharmaceutical liquids, comprising:
   a housing;
   an outlet opening; and
   an outlet valve assigned to the outlet opening, the outlet valve having a closed position to prevent fluid flow therethrough and an open position to allow fluid flow therethrough;
   wherein the outlet valve comprises:
      a valve opening and a valve pin, the valve pin closing the valve opening in the closed position and releasing the valve opening in the open position;
      a valve body, which has either the valve pin or the valve opening and which is displaceable at least partially with respect to the housing of the liquid dispenser to thereby allow for transfer of the outlet valve between the closed position and the open position; and
      a pressure chamber arranged upstream of the valve opening and delimited to one side by a valve plate of the valve body, the valve body being displaceable at least in portions by application of pressure at the valve plate by liquid in the pressure chamber, such that the valve pin and the valve opening are thereby displaced relative to one another;
   wherein at least one portion of the valve plate which is in contact with liquid in the pressure chamber comprises an elastic cycloolefin copolymer or a combination of an elastic cycloolefin copolymer and polypropylene; and
   wherein the valve body includes a deformable portion and a fixing region which is fixed immovably in relation to the housing for allowing the valve opening or the valve pin to be displaced with respect to the housing.

14. The liquid dispenser as claimed in claim 13, wherein the valve opening is provided immovably in relation to the housing and the valve body has the valve pin, the valve pin being displaceable by at least partial displacement of the valve plate with respect to the valve opening.

15. The liquid dispenser as claimed in claim 14, wherein at least one portion of the valve plate and the valve pin are in the form of an integral component.

16. The liquid dispenser as claimed in claim 13, wherein the valve plate is provided with a circumferential deformation region, in which the valve plate has a thinner form than in regions adjoining radially on an inside and outside.

17. The liquid dispenser as claimed in claim 13, wherein the outlet valve has a valve spring, which subjects the valve pin and the valve opening to force in a direction of the closed position.

\* \* \* \* \*